United States Patent
Jenkins et al.

(10) Patent No.: US 6,708,572 B2
(45) Date of Patent: Mar. 23, 2004

(54) PORTAL TRACE DETECTION SYSTEMS FOR DETECTION OF IMBEDDED PARTICLES

(75) Inventors: Anthony Jenkins, North Reading, MA (US); William J. McGann, Raynham, MA (US); Kevin J. Perry, Pelham, NH (US)

(73) Assignee: General Electric Company, Schenectady, NY (US)

( * ) Notice: Subject to any disclaimer, the term of this patent is extended or adjusted under 35 U.S.C. 154(b) by 113 days.

(21) Appl. No.: 10/033,874

(22) Filed: Dec. 20, 2001

(65) Prior Publication Data

US 2002/0078767 A1 Jun. 27, 2002

Related U.S. Application Data

(60) Provisional application No. 60/257,441, filed on Dec. 22, 2000.

(51) Int. Cl.$^7$ ................................................. G01N 1/22
(52) U.S. Cl. ................. 73/864.33; 73/28.04; 73/863.21
(58) Field of Search ........................ 73/864.33, 863.21, 73/28.01, 28.04

(56) References Cited

U.S. PATENT DOCUMENTS

| | | | | |
|---|---|---|---|---|
| 5,109,691 A | * | 5/1992 | Corrigan et al. ....... | 73/28.01 X |
| 5,491,337 A | * | 2/1996 | Jenkins et al. ............... | 250/287 |
| 5,585,575 A | * | 12/1996 | Corrigan et al. ..... | 73/864.33 X |
| 5,915,268 A | * | 6/1999 | Linker et al. .......... | 73/28.01 X |
| 6,073,499 A | * | 6/2000 | Settles ..................... | 73/864.81 |
| 6,334,365 B1 | * | 1/2002 | Linker et al. ............. | 73/864.81 |
| 6,375,697 B2 | * | 4/2002 | Davies ........................ | 55/340 |
| 2003/0085348 A1 | * | 5/2003 | Megerle ..................... | 250/287 |

* cited by examiner

Primary Examiner—Thomas P. Noland
(74) Attorney, Agent, or Firm—Anthony J. Casella; Gerald E. Hespos

(57) ABSTRACT

A portal trace detection apparatus is provided for detecting minute particles of interest, such as traces of narcotics, explosives and other contraband. The apparatus includes a portal through which a human suspect will pass. A detection apparatus is disposed at least partly in the ceiling of the portal, and hence above the human subject in the portal. Particles of interest will be entrained in the human thermal plume that exists in the boundary layer of air adjacent the suspect, and will flow upwardly from the suspect to the detection apparatus in the ceiling of the portal. The portal includes a plurality of vertically aligned arrays of air jets. The air jets are fired sequentially from bottom to top to produce short bursts of air sufficient to disturb the clothing of the suspect and to dislodge particles of interest from the clothing. The dislodged particles of interest are entrained in the air in the human thermal plume and are transported upwardly to the detector.

28 Claims, 1 Drawing Sheet

PORTAL TRACE DETECTION SYSTEMS FOR DETECTION OF IMBEDDED PARTICLES

Figure 1:
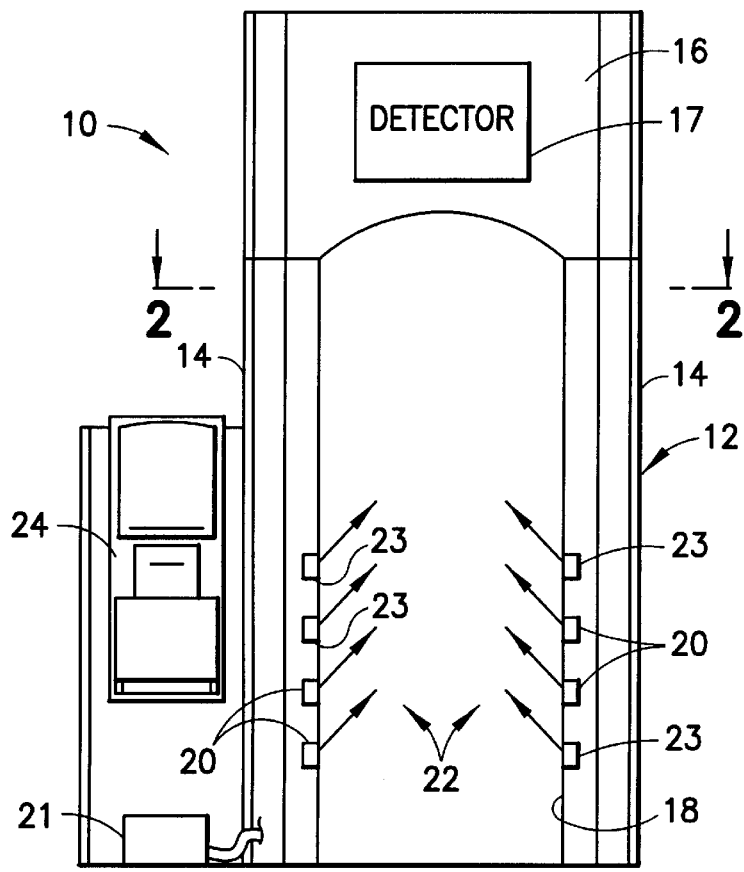
Figure 2:
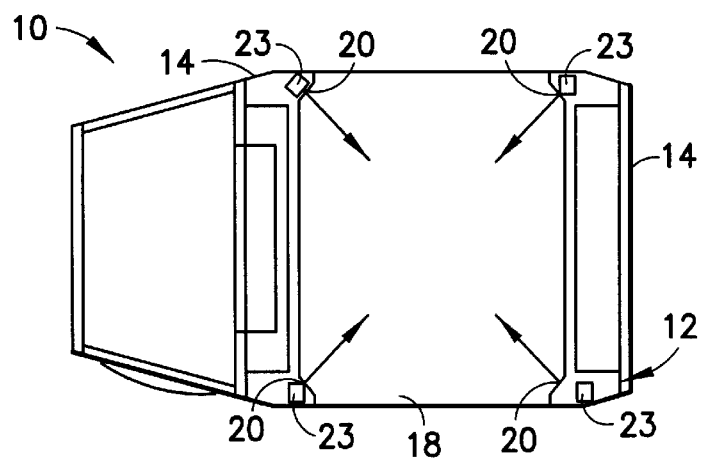

This application is a non-provisional of U.S. Provisional Patent Appl. No. 60/257,441 filed Dec. 22, 2000.

BACKGROUND OF THE INVENTION

1. Field of the Invention

The subject invention relates to a detection apparatus for dislodging particles from clothing and skin of a person and then testing the dislodged particles for the presence of substances of interest.

2. Description of the Related Art

Detection systems exist for detecting traces of materials, such as narcotics and explosives. Such systems are marketed by Ion Track Instruments, Inc. and are shown, for example, in U.S. Pat. No. 5,491,337.

Prior art detection systems rely upon the fact that trace amounts of contraband will be transferred to the body of a person who handled the contraband, and subsequently will be transferred from the body to any article that the person may carry. These trace amounts of contraband may be collected for analysis by wiping a small sheet of appropriate material across a purse, suitcase or other article that has been handled by a suspect. The prior art sheet then is inserted into a prior art detection apparatus which tests for the presence of certain contraband.

Attempts have been made to provide such contraband testing without physically contacting the suspect or articles that the suspect may be transporting. Several such prior art devices employ a portal through which the suspect will walk. Most of these prior art devices create a flow of air in the portal in an effort to entrain the particles of interest in a continuously flowing air stream. The air stream then is directed to a detector which attempts to identify the presence of particles of interest. Unfortunately, the prior art apparatus draws a significant volume of air from outside the portal, and hence substantially dilutes the concentration of particles of interest in the air stream that is directed to the detector.

U.S. Pat. No. 6,073,499 shows a recent improvement with respect to portals for detecting the presence of contraband on a suspect. More particularly, U.S. Pat. No. 6,073,499 discloses a portal detection system that relies upon the fact that a boundary of air adjacent to a human being is heated by the body. The heated air in this boundary layer is less dense than air further from the suspect, and hence will flow upwardly. Thus, a human thermal plume is created naturally around the human suspect. Particles of interest will be entrained in this thermal plume and will rise upwardly around the body. The portal system shown in U.S. Pat. No. 6,073,499 relies upon this natural phenomena by providing a fan or other air flow generator at a location above the suspect and operating at a speed to substantially match the airflow rate of the naturally-occurring human thermal plume. Thus, the fan or other such device shown in U.S. Pat. No. 6,073,499 merely directs the naturally occurring human thermal plume to a detector without drawing significant volumes of ambient air into the detector. Thus, the concentration of particles of interest is significantly higher than the concentration in prior art portals that create a significant artificial airflow in an effort to entrain and transport the particles of interest.

The prior art detection portal disclosed in U.S. Pat. No. 6,073,499 is particularly effective for detecting trace amounts of contraband that may have been deposited on the skin of a suspect. However, microscopic particles of contraband also are very likely to be trapped in the clothing of a suspect. The natural thermal plume existing in the boundary layer surrounding a human suspect may not be capable of dislodging particles of interest from the clothing. Of course, most of a human suspect will be covered by clothing. Hence, the efficiency of the system disclosed in U.S. Pat. No. 6,073,499 may be limited somewhat by the tendency of particles of interest to be trapped in the clothing of the human suspect passing through the portal.

Some prior art systems, including the system shown in U.S. Pat. No. 6,073,499 suggest the use of air jets to dislodge particles of interest from clothing. However, air jets can create turbulence that may disrupt the efficient upward flow of air in the natural thermal plume surrounding the human suspect. Additionally, air jets have the potential of creating air flow patterns that will draw significant volumes of air from the ambient surroundings, thereby reducing the concentration of the particles of interest in the flow of air directed to the detector.

In view of the above, an object of the subject invention to provide a portal trace detection system that is capable of detecting embedded particles, such as particles embedded in clothing of a human suspect passing through the portal.

SUMMARY OF THE INVENTION

The subject invention is directed to a portal detection system that relies primarily upon the upwardly flowing human thermal plume. The portal includes an inspection apparatus with an inlet disposed above the area of the portal where the human suspect will stand. The inlet may be in communication with a fan or other such device for generating an air flow. Preferably, the fan or other such apparatus will operate to generate an air flow that substantially matches the air flow rate in a typical human thermal plume. For example, the air flow rate in close proximity to the human body is approximately 0.5 meter per second, and the fan may function to substantially match this air flow speed and volumetric rate of flow.

The portal of the subject invention may be similar to the portal shown in U.S. Pat. No. 6,073,499 in most relevant respects. However, the portal of the subject invention is supplemented by a plurality of air jets disposed at locations that will extend approximately from knee level to chest level of a typical human subject passing through the portal. Tests have shown that this area of the body carries most contamination after handling a contraband material.

The array of air jets preferably comprises a plurality of vertical lines of air jets disposed at a plurality of different sides on the portal and directed inwardly and upwardly in the portal. For example, four vertical lines of air jets may be disposed respectively at the corners of the portal. The air jets in each line may be separated from one another by about 300 mm, and preferably are aligned to the vertical at an angle of between 30°–60°.

The jets may be connected to a high pressure (40–100 psi) air supply and may be operated sequentially by solenoid valves that are connected to and operated by a controller. Each jet is operative to deliver a short puff of air which disturbs the clothing of the human suspect sufficiently to release trapped particles. The air flow created by the jets necessarily disturbs the body plume somewhat, and hence conceivably could cause a turbulence that could direct particles of interest out of the portal. However, the effect of the jets on the human thermal plume can be minimized substantially by operating each jet only for a very short duration. Thus, each jet functions essentially like a smoke ring with a local disturbance, but a minimum effect on air flow patterns in the human thermal plume. Furthermore, the effect of the short puffs of air produced by the jet can be used cooperatively with the human thermal plume by actuating the jets sequentially from bottom to top in each of the vertical arrays of jets. The jets preferably are switched on for about 10–80 ms, and each level of jets is switched off before the next level is switched on. It has been determined that longer periods of operation for the respective jets adversely affects the human thermal plume without significantly increasing the release of particles from the clothing of the human suspect passing through the portal.

The portal apparatus of the subject invention provides still a further advantage. In particular, it has been determined that small dander particles that are given off from the skin gradually migrate into the clothing. These dander particles can act as vapor traps for very low volatility materials, such as explosives and narcotics which may be hidden under the clothing of under the human subject passing through the portal. These dander particles are released by the jets, and hence become entrained in the human thermal plume. More particularly, the dander particles effectively become tiny traps that are released by the jets and transported in the human thermal plume to the detection system where the trapped vapors are desorbed. Thus, the incorporation of the jets into the portal detection system creates the possibility of detecting vapors that normally would be below the threshold of sensitivity of the system.

It also has been determined that particles of interest often affix themselves to the hood or ceiling of the portal due to static electricity, in much the same way that dust accumulates on a television screen. This phenomenon can be reduced or eliminated by coating the hood or ceiling with an anti-static material. Thus, fewer particles become affixed to the hood, and sensitivity is increased.

BRIEF DESCRIPTION OF THE DRAWINGS

FIG. 1 is a front view of a portal detection apparatus in accordance with the subject invention.

FIG. 2 is a cross-sectional view taken along line 2—2 in FIG. 1.

DETAILED DESCRIPTION OF THE PREFERRED EMBODIMENT

A portal detection system in accordance with the subject invention is identified generally by the numeral 10 in FIGS. 1 and 2. The portal detection system 10 is similar to the portal detection system disclosed in U.S. Pat. No. 6,073,499. In particular, the portal detection system 10 includes a portal 12 having a plurality of sidewalls 14, a plastic ceiling or hood 16 and a passage 18 extending between the sidewalls 14 and beneath the ceiling 16. The ceiling 16 preferably is made from or coated with an anti-static material such as KYDEX T as manufactured by Kleerdex. The anti-static material reduces or eliminates the electrostatic accumulation of particles of interest on the ceiling, and hence improves sensitivity. The ceiling 16 includes an inlet with a fan for producing an air flow that substantially matches the air flow rate provided by the human thermal plume. The ceiling 16 further includes at least portions of detection system 17. The detector of the subject invention is not disclosed herein. However, the detector may be an ion trap mobility spectrometer as disclosed in U.S. Pat. No. 5,491,337. Additionally, various structural and operational features of the portal 12 are as disclosed in U.S. Pat. No. 6,073,499. The disclosures of these two patents are incorporated herein by reference.

The apparatus 10 of FIGS. 1 and 2 further includes a plurality of air jets 20. The jets are arranged to define four linear jet arrays 22 with the jets 20 in each array 22 being vertically aligned. The jets 20 preferably are disposed in the portal 12 to extend from a lower location approximately at knee level (e.g., 1–2 feet from the ground) to an upper location approximately at chest level (e.g., 4–5 feet from the ground). Each jet 20 is disposed to direct a short puff of air inwardly and upwardly into the passage 18 of the portal 12. More particularly, as shown most clearly in FIG. 1, the jets 20 are aligned at an acute angle of approximately 30°–60° to the vertical. The jets 20 communicate with a supply 21 of high pressure air in the range of 40–100 psi and preferably 80 psi. The jets 20 include solenoid valves 23 that communicate with and are controlled by a controller 24 to operate sequentially. More particularly, the controller 24 functions to fire the respective jets 20 sequentially from bottom to top. Each jet 20 is switched on for about 10–100 ms and preferably about 50 ms. Each jet 20 then is switched off for about 100 ms before the next higher jet 20 is switched on. The jets 20 function to disturb the clothing of the human subject in the passage 18 sufficiently to dislodge particles of interest that may be trapped in the clothing of the suspect. However, the short puffs of air are controlled to achieve minimum disruption and minimum dilution of the human thermal plume. The dislodged particles then are entrained in the human thermal plume that exists adjacent the human subject. The air in the human thermal plume, including the particles of interest that are dislodged from the clothing are directed to the detector substantially as disclosed in U.S. Pat. No. 6,073,499.

In use, the suspect is instructed to enter the portal 12. Visual signals or voice prompts will ask the suspect to remain in the portal 12 for about 5–10 seconds. The jets 20 will then fire sequentially from bottom to top. More particularly, the four lower tier jets 20 will fire simultaneously for about 50 ms. There then will be a pause of about 100 ms, and the four jets 20 in the second tier will fire for about 50 ms. This process will continue until the four jets 20 in the tip tier have fired. Particles displaced by the jets 20 will be entrained in the human thermal plume and will flow naturally upward through the hood-shaped ceiling 16. After about 5–10 seconds, the suspect will be instructed to exit the portal 12.

What is claimed is:

1. A portal trace detection system comprising a portal having a plurality of sidewalls and a passage between the sidewalls, a ceiling connecting the sidewalls and disposed above the passage, a particle detection apparatus having an inlet in communication with the passage for receiving air flowing adjacent to a human suspect in the passage of the portal, a plurality of air jets disposed in the portal and aligned for directing short puffs of air into the passage of the portal, control means communicating with the air jets for controlling the air jets to fire at least one short burst of air for dislodging particles of interest trapped in clothing of a human suspect in the passage.

2. The portal trace detection system of claim 1, wherein each said jet is aligned to project inwardly and upwardly into the passage of the portal.

3. The portal trace detection system of claim 2, wherein each said jet is aligned at an acute angle of approximately 30°–60° to a vertical axis.

4. The portal trace detection system of claim 1, wherein the plurality of jets comprise a plurality of vertical arrays of jets.

5. The portal trace detection system of claim 4, wherein the passage has a floor, each said vertical array of jets having a lower jet disposed between approximately 1–2 feet from the floor and an upper jet disposed between approximately 4–5 feet from the floor.

6. The portal trace detection system of claim 5, wherein the control means comprises means for firing short bursts of air sequentially from a lower location to an upper location in each said array.

7. The portal trace detection system of claim 4, wherein the linear arrays of jets comprise two opposed pairs of linear arrays, a first of said pairs being angularly aligned to a second of said pairs by a approximately 90°.

8. The portal trace detection system of claim 1, further comprising a supply of compressed air, the jets being in communication with the supply of compressed air and comprising valve means for generating bursts of air sufficiently strong for dislodging particles of interest from clothing of the human suspect.

9. The portal trace detection system of claim 1, further comprising a supply of air having a pressure of between 40 psi and 100 psi.

10. The portal trace detection system of claim 1, further comprising solenoid valves for controlling direction of air to the respective air jets.

11. The portal trace detection of claim 1, wherein the ceiling comprises an antistatic material.

12. The portal trace detection system of claim 1, wherein the control means comprises means for firing short bursts of air sequentially from a lower location to an upper location in the portal.

13. A portal trace detection system comprising a portal having a plurality of sidewalls and a passage between the sidewalls, a ceiling connecting the sidewalls and disposed above the passage, a particle detection apparatus having an inlet in communication with the passage for receiving air flowing adjacent to a human suspect in the passage of the portal, a plurality of vertical arrays of air jets disposed in the portal and aligned for directing short puffs of air into the passage of the portal, air supply means for supplying air having a pressure of between 40 psi and 100 psi, and control means communicating with the air supply means and the air jets for firing bursts of air with durations of between 10 ms and 100 ms, said bursts of air being fired by the control means sequentially from lower air jets to upper air jets in each said vertical array of air jets, whereby said short bursts of air dislodge particles of interest trapped in clothing of a human suspect in the passage.

14. The portal trace detection system of claim 13, wherein the control means further comprises means for generating a pause between each burst of air in each of the vertical arrays of air jets.

15. A portal trace detection system comprising a portal having a plurality of sidewalls and a passage between the sidewalls, a ceiling connecting the sidewalls and disposed above the passage, a particle detection apparatus having an inlet in communication with the passage for receiving air flowing adjacent to a human suspect in the passage of the portal, a plurality of air jets disposed in the portal and aligned for directing short puffs of air into the passage of the portal, a controller communicating with the air jets for controlling the air jets to fire at least one short burst of air for dislodging particles of interest trapped in clothing of a human suspect in the passage.

16. The portal trace detection system of claim 15, wherein each said jet is aligned to project inwardly and upwardly into the passage of the portal.

17. The portal trace detection system of claim 16, wherein each said jet is aligned at an acute angle of approximately 30°–60° to a vertical axis.

18. The portal trace detection system of claim 17, wherein the plurality of jets comprise a plurality of vertical arrays of jets.

19. The portal trace detection system of claim 18, wherein the passage has a floor, each said vertical array of jets having a lower jet disposed between approximately 1–2 feet from the floor and an upper jet disposed between approximately 4–5 feet from the floor.

20. The portal trace detection system of claim 19, wherein the controller is operative for firing short bursts of air sequentially from a lower location to an upper location in each said array.

21. The portal trace detection system of claim 18, wherein the linear arrays of jets comprise two opposed pairs of linear arrays, a first of said pairs being angularly aligned to a second of said pairs by a approximately 90°.

22. The portal trace detection system of claim 15, further comprising a supply of compressed air, the jets being in communication with the supply of compressed air and comprising valves for generating bursts of air sufficiently strong for dislodging particles of interest from clothing of the human suspect.

23. The portal trace detection system of claim 15, further comprising a supply of air having a pressure of between 40 psi and 100 psi.

24. The portal trace detection system of claim 15, further comprising solenoid valves for controlling direction of air to the respective air jets.

25. The portal trace detection of claim 15, wherein the ceiling comprises an antistatic material.

26. The portal trace detection system of claim 15, wherein the controller is operative for firing short bursts of air sequentially from a lower location to an upper location in the portal.

27. A portal trace detection system comprising a portal having a plurality of sidewalls and a passage between the sidewalls, a ceiling connecting the sidewalls and disposed above the passage, a particle detection apparatus having an inlet in communication with the passage for receiving air flowing adjacent to a human suspect in the passage of the portal, a plurality of vertical arrays of air jets disposed in the portal and aligned for directing short puffs of air into the passage of the portal, an air supply for supplying air having a pressure of between 40 psi and 100 psi, and a controller communicating with the air supply and the air jets for firing bursts of air with durations of between 10 ms and 100 ms, said bursts of air being fired by the controller sequentially from lower air jets to upper air jets in each said vertical array of air jets, whereby said short bursts of air dislodge particles of interest trapped in clothing of a human suspect in the passage.

28. The portal trace detection system of claim 27, wherein the controller is operative for generating a pause between each burst of air in each of the vertical arrays of air jets.

* * * * *